United States Patent
Kretschmer et al.

(10) Patent No.: US 6,299,614 B1
(45) Date of Patent: Oct. 9, 2001

(54) DEVICE FOR STABILIZING VERTEBRA BODIES OF THE SPINAL COLUMN

(75) Inventors: Peter Kretschmer, Bruchköbel; Uwe Siedler, Alzenau, both of (DE)

(73) Assignee: Signus Medizintechnik GmbH, Alzenau (DE)

( * ) Notice: Subject to any disclaimer, the term of this patent is extended or adjusted under 35 U.S.C. 154(b) by 0 days.

(21) Appl. No.: 09/538,387

(22) Filed: Mar. 29, 2000

(30) Foreign Application Priority Data

Mar. 29, 1999 (DE) .............................. 199 14 232

(51) Int. Cl.⁷ .............................. A61B 17/68; A61B 17/70
(52) U.S. Cl. .................................. 606/61; 606/60
(58) Field of Search ................. 606/60, 61, 72

(56) References Cited

U.S. PATENT DOCUMENTS

| | | | |
|---|---|---|---|
| 4,987,892 | * 1/1991 | Krag et al. | 606/61 |
| 5,380,325 | * 1/1995 | Lahille et al. | 606/61 |
| 5,507,746 | * 4/1996 | Lin | 606/61 |
| 5,681,312 | * 10/1997 | Yuan et al. | 606/61 |
| 5,938,663 | * 8/1999 | Petreto | 606/61 |
| 5,947,965 | * 9/1999 | Bryan | 606/61 |
| 5,980,521 | * 11/1999 | Montague et al. | 606/61 |
| 6,036,693 | * 3/2000 | Yuan et al. | 606/61 |
| 6,123,706 | * 9/2000 | Lange | 606/61 |
| 6,136,003 | * 10/2000 | Hoeck et al. | 606/61 |
| 6,179,838 | * 1/2001 | Fiz | 606/61 |
| 6,187,005 | * 2/2001 | Brace et al. | 606/61 |
| 6,217,578 | * 4/2001 | Crozet et al. | 606/61 |

* cited by examiner

*Primary Examiner*—Paul J. Hirsch
*Assistant Examiner*—Michael B. Priddy
(74) *Attorney, Agent, or Firm*—Friedrich Kueffner

(57) ABSTRACT

A device for stabilizing vertebrae of a spinal column has a stabilizing rod and clamps each having a receiving bore for receiving the stabilizing rod. The clamps each have a first leg and a second leg. Each leg has a transverse bore extending transversely to the receiving bore. The transverse bores of the first and second legs are aligned with one another. Screws having a first threaded portion for threadingly engaging a vertebra are provided. The screws have a screw head remote from the first threaded portion and a second threaded portion projecting from the screw head in a direction away from the first threaded portion. At least the transverse bore of the first leg of the clamps have a bore insert member inserted in the transverse bore and resting against the outer surface of the first leg and having an eccentric insert bore. The second threaded portion of the screws penetrate the eccentric insert bore. The eccentric insert bore causes the screws to have a slanted position relative to the clamp and the stabilizing rod. Clamping nuts engage the second threaded portion and, when tightened on the second threaded portion, force the first and second legs of the clamps toward one another thereby securing the stabilizing rod in the receiving bore.

12 Claims, 3 Drawing Sheets

DEVICE FOR STABILIZING VERTEBRA BODIES OF THE SPINAL COLUMN

BACKGROUND OF THE INVENTION

1. Field of the Invention

The invention relates to a device for stabilizing vertebra bodies of the spinal column.

2. Description of the Related Art

Such stablizing devises have screws that can be threaded with thier threaded portion through the vertebra pedicles of adjacent vertebra bodies and have a stabilizing rod connecting the screws wherein a clamp is positioned between each screw and the rod.

It is easily understood that the spinal column is subjected to extremly high forces. The stabilizing device must be suitable to recieve these forces and to transmit them.

SUMMARY OF THE INVENTION

It is an object of the present invention to improve the device of the aforementioned kind in a simple and effective manner such that a connection is provided between the screws and the stabilizing rod connecting them that provides angular stability despite the great force loading acting thereon.

In accordance with the present invention, this is achieved in that the screws have a screw head, at a side facing away from the threaded vertebra-engaging portion, and a threaded clamping portion projecting past the screw head. The threaded clamping portion can penetrate the transverse bores in the two legs of the clamp which is slidably positioned on the stabilizing rod but can be fastened thereto. The threaded clamping portion can be loaded by a clamping nut such that the two legs of the clamp are brought closer to one another. At least one of the two transverse bores has coordinated therewith a bore insert member which is supported on the leg and has an eccentric insert bore. Its position relative to the transverse bore determines a more or less slanted position of the clamp and thus of the stabilizing rod relative to the screw.

The device elements which are clamped to one another and thus form the device according to the invention allow, because of their configuration, in an advantageous manner a plurality of different fixed positions of the screws relative to one another. It was found to be very beneficial with regard to the desired stability of the device for its use to provide the insert-receiving transverse bore of the leg of the clamp with a diameter which, in comparison to the transverse bore of the other leg, is greater and tapers in the direction toward the other leg. Furthermore, the outer diameter and the shape of the bore insert member are matched to those of the transverse bore.

Expediently, the eccentric insert bore of the bore insert member is positioned at an acute angle relative to the central axis of the insert and the acute angle has a magnitude of up to 20°. In this way, it is possible to provide a large number of relative positions of the screws to one another with very fine adjustment.

In order to ensure an especially safe clamping of the bore insert member relative to the clamp, it is very advantageous when the insert member is provided with a radial slot extending from the eccentric insert bore to the outer mantle surface of the bore insert member. The radial slot expediently extends in the area of the bore insert member which has the greatest spacing between the eccentric insert bore and the outer mantle surface. This provides an optimal adaptability of the position of the bore insert member to the respective requirements because the area with the smallest wall thickness of the bore insert member is positioned opposite the radial slot, and this configuration provides a sufficient flexibility of the bore insert member.

A close fit and contact of the cooperating surfaces of the clamping leg and the screw will advantageously result when the other leg of the clamp has a recess which is matched to the diameter of the transverse bore, diminishes in the direction toward the edge of the transverse bore, and whose wall is configured to be the contact surface for the screw head. Expediently, in a further advantageous embodiment, the screw head is spherically convex and the wall of the recess providing the contact surface for the screw head is correspondingly spherically concave.

An advantageously defined positioning of the bore insert member relative to the corresponding clamp leg can be achieved when the bore insert member is provided with a radially projecting rim portion at its side facing away from the other leg of the clamp which is supported in a matching partially recessed support surface in the leg of the clamp.

Usually, the outer leg surfaces of the clamp which face one another extend in parallel planes and are positioned at a right angle relative to the central axis of the receiving bore for the stabilizing rod and thus to the axis of the stabilizing rod.

However, a greater range of angular positions can be achieved according to a further embodiment of the invention by positioning the parallel outer leg surfaces of the clamp facing one another such that they are positioned at an angle which differs from a right angle by up to ±10° relative to the central axis of the receiving bore and the axis of the stabilizing rod. In this manner, the slanted positioning range of the screws in relation to the axial plane of the stabilizing rod can be increased by 10° beyond the maximum achievable slanted position resulting from the eccentric arrangement of the eccentric insert bore of the bore insert member. Accordingly, the adjusting range can be increased without compromising the stability of the respectively selected and fixed adjustment position.

BRIEF DESCRIPTION OF THE DRAWING

The drawing illustrates the device of the present invention on a scale of approximately 5:1. In the drawing.

DESCRIPTION OF THE PREFERRED EMBODIMENTS

Figure 1:
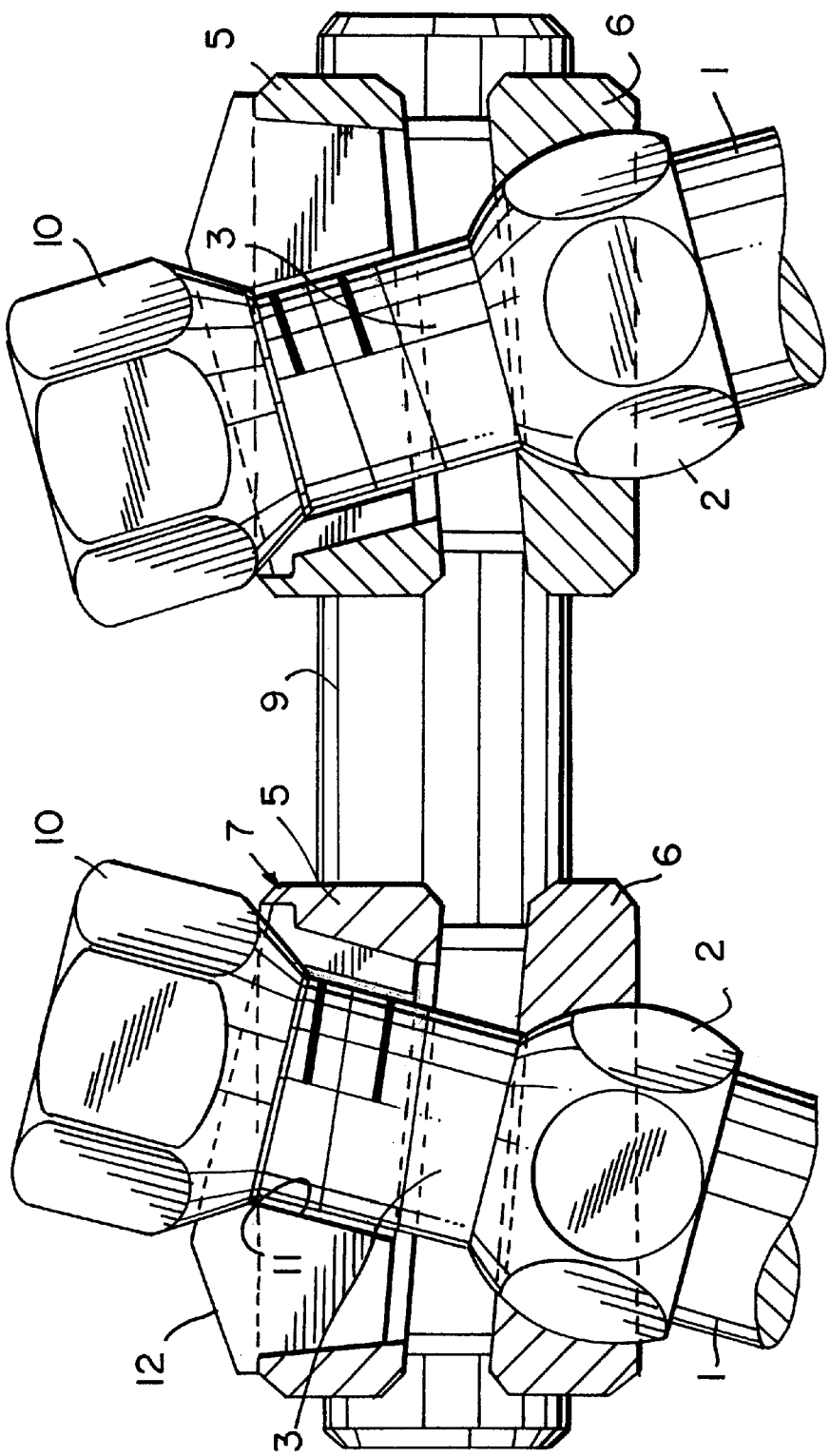
FIG. 1 is an end view of the device according to the invention in a direction onto the respective clamp legs, partially in section in the area of the transverse bores receiving the screws.

The device illustrated in the drawing for stabilizing vertebra bodies of a spinal column employs preferably screws 1 extending through the vertebra pedicles of adjacent vertebra bodies with their respective threaded vertebra-engaging portion. The vertebra bodies and vertebra pedicles are not shown in the drawing. Shown is only the screw head 2 positioned remote from the threaded vertebra-engaging portion (not shown) and a threaded clamping portion 3 projecting past the screw head 2 away from the threaded vertebra-engaging portion. This threaded clamping portion 3 can be guided through the transverse bores 4 provided in the two legs 5, 6 of a clamp 7. The clamp 7 has a round receiving bore 8 in which, as illustrated in FIG. 1, a stabilizing rod 9 is seated. The clamp 7 seated on the stabilizing rod 9 can be rotated about the rod axis and axially moved along the rod 9.

A clamping nut 10 can be threaded onto the threaded clamping portion 3 of each screw 1. With their assistance, the two legs 5, 6 of the clamp 7 can be loaded (moved) toward one another in order to secure and fasten the stabilizing rod 9 in the clamp 7.

FIG. 1 shows clearly that in one of the two transverse bores 4 a bore insert member 12 is arranged which is supported on the leg 5 and has an eccentric insert bore 11. The position of the bore insert member 12 relative to the transverse bore 4 in the leg 5 can be changed and adjusted at will. In this way, a more or less slanted position of the clamp 7 and thus of the stabilizing rod 9 relative to the screw 1 is determined.

Figure 2:
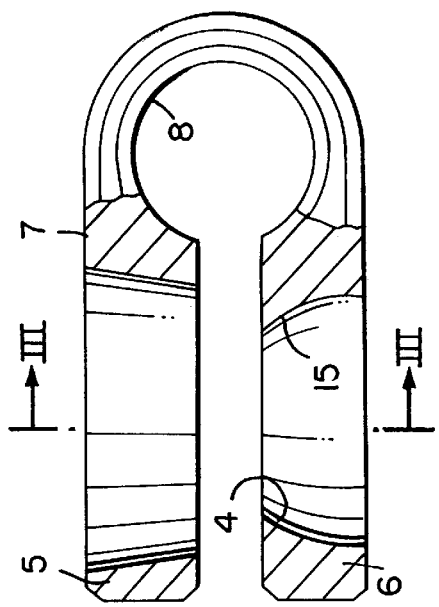
FIG. 2 is a sectional view of the clamp.
Figure 4:
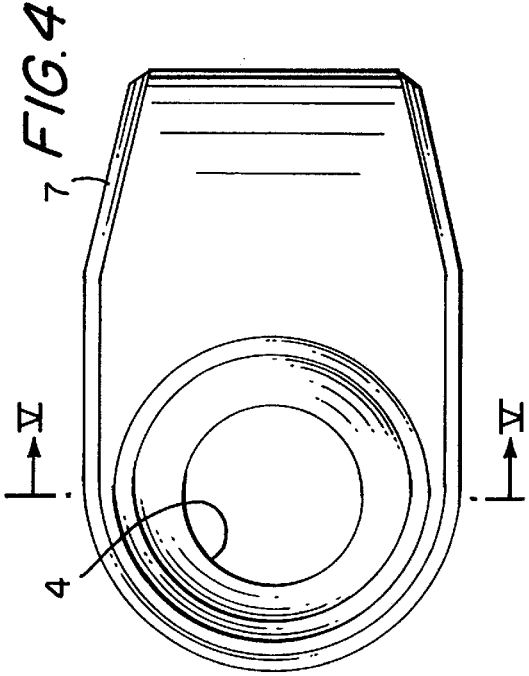
FIG. 4 is a plan view onto the clamp of FIG. 2.
Figure 6:
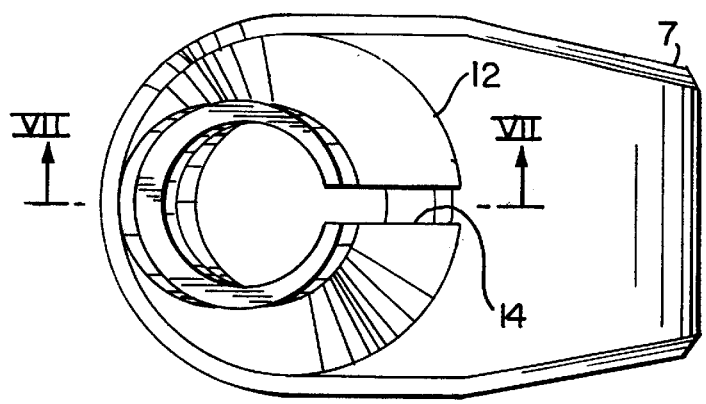
FIG. 6 is a plan view of a second embodiment according to the invention showing a clamp with inserted bore insert member.
Figure 7:
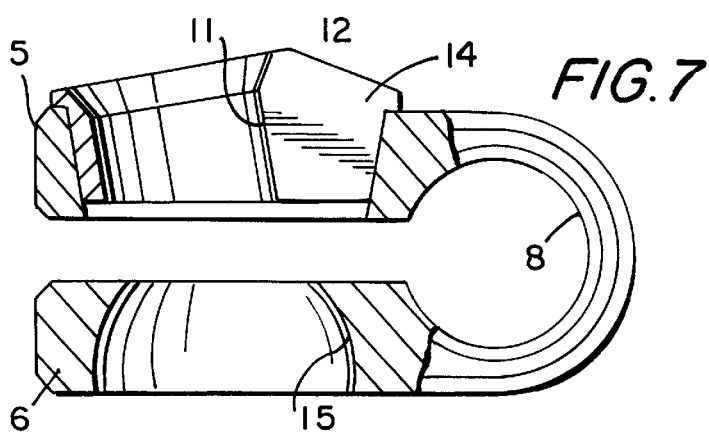
FIG. 7 is a side view of the clamp, partially in axial section, along line VII—VII of FIG. 6.
Figure 8:
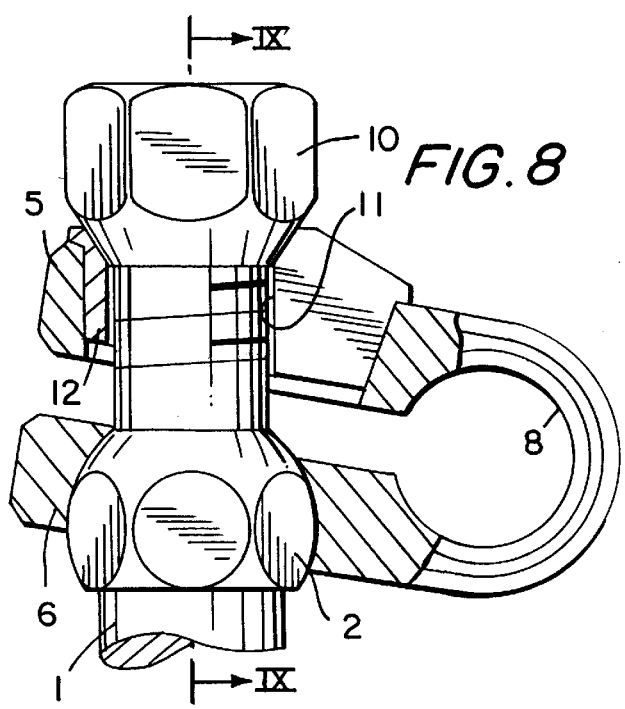
FIG. 8 is a side view of a clamp with bore insert member, screw, and clamping nut positioned on the threaded clamping portion of the screw, partially in section.

FIG. 2 shows that the transverse bore 4 of the leg 5 of the clamp 7 for receiving the bore insert member 12 has in comparison to the transverse bore 4 of the other leg 6 a greater diameter which slightly tapers toward the transverse bore 4 in the leg 6. The outer diameter and the conical shape of the bore insert member 12 are matched to the shape of this transverse bore 4 of the leg 5. Due to this matched shaping, it is possible to rotate the bore insert member 12, which is penetrated by the threaded clamping portion 3 of the screw 1, to such an extent about its center axis 13 relative to the transverse bore 4 in the leg 5 of the clamp 7 before tightening the clamping nut 12 that the desired position of the clamp 7 and thus of the stabilizing rod 9 is obtained. By subsequently tightening the clamping nut 10, not only the position of the bore insert member 12 together with the screw 1 relative to the clamp 7 is determined but also that of the clamp 7 in relation to the stabilizing rod 9. The conical transverse bore 4 of leg 5, in which the bore insert member 12 is received, has an inner bore surface on which the conical outer surface of the bore insert member 12 comes to rest, and this inner bore surface is machined to provide a rough surface, for example, in the form of ribbing. This configuration ensures an especially safe fixation of the angular position of the bore insert 12 in the transverse bore 4 which is not canceled even when high loads act on the clamp and the screw.

Figure 3:
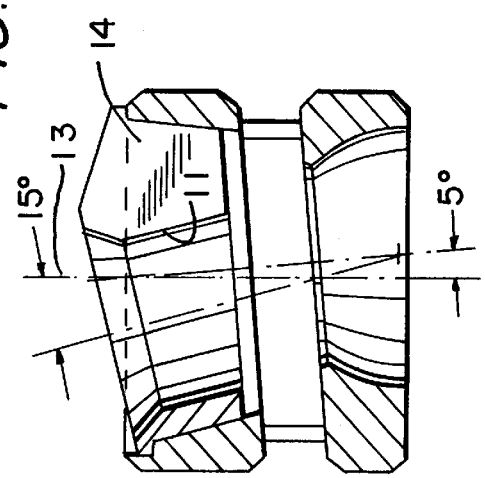
FIG. 3 is a sectional view of the clamp along line III—III of FIG. 2, with inserted bore insert member.

An especially fine adjustment is ensured in that the eccentric insert bore 11 of the bore insert member 12 is positioned at an angle relative to the center axis 13 of the bore insert member 12 which in practice has a magnitude of up to 15° and in extreme cases of up to 20°. The adjusting and clamping properties of the device are furthermore improved in that the bore insert member 12 is provided with a radial slot 14 which extends from the eccentric insert bore 11 to the conical outer mantle surface of the member 12 which rests against the inner rough surface of the transverse bore 4 in the leg 5. Especially FIG. 3 shows that the radial slot 14 extends through that portion of the insert member 12 which has the greatest spacing between the eccentric insert bore 11 and the conical outer mantle surface. In this way, the flexibility of the bore insert member 12 is advantageously increased.

The other leg 6 of the clamp 7 has a recess 15 matched to the diameter of the transverse bore 4 and diminishing in the direction of the transverse bore edge. The wall of this recess is designed as a contact surface for the screw head 2. As can be seen in the drawing, the screw head 2 is spherically convex and the contact surface of the recess 15 has a matching spherically concave shape.

Figure 5:
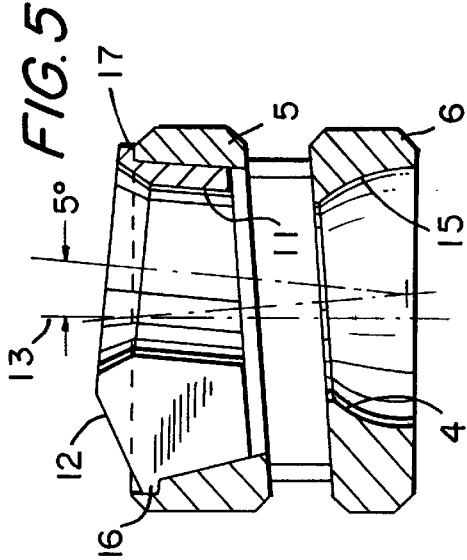
FIG. 5 is a sectional view along line V—V of FIG. 4.
Figure 9:
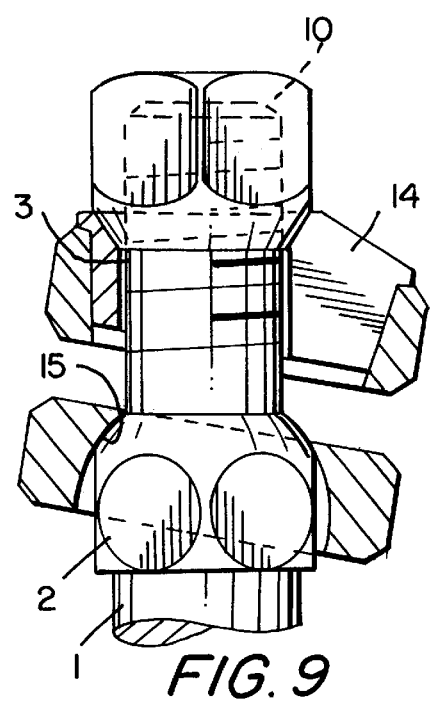
FIG. 9 is an end view of the clamp, partially in section, according to the line IX—IX of FIG. 8.

The side of the bore insert member 12 facing away from the leg 6 of the clamp 7 has a radial projecting rim portion 16 which is supported on the flat outer surface of the leg 5 (FIG. 9) or in a correspondingly shaped, partially recessed support surface 17 within the leg 5 of the clamp 7 (FIG. 5).

In the simplest case, the outer leg surfaces of the clamp 7 facing one another are positioned in planes parallel to one another and are positioned at a right angle to the central axis of receiving bore 8, respectively, the axis of the stabilizing rod 9. However, the adjusting range of the device can be enlarged advantageously when positioning the facing outer leg surfaces extending parallel to one another at a slant angle relative to the central axis of the receiving bore 8, respectively, the axis of the stabilizing rod 9 that deviates from a right angle by up to ±5° and in extreme cases even up to ±10°.

While specific embodiments of the invention have been shown and described in detail to illustrate the inventive principles, it will be understood that the invention may be embodied otherwise without departing from such principles.

What is claimed is:

1. A device for stabilizing vertebrae of a spinal column, the device comprising:

a stabilizing rod;

clamps each having a receiving bore configured to receive the stabilizing rod;

the clamps each having a first leg and a second leg;

each one of the first and second legs having a transverse bore extending transversely to the receiving bore, wherein the transverse bores of the first and second legs of the clamps are aligned with one another;

screws having a first threaded portion configured to threadingly engage a vertebra;

the screws having a screw head remote from the first threaded portion and a second threaded portion projecting from the screw head in a direction away from the first threaded portion;

at least the transverse bore of the first leg of the clamps having a bore insert member inserted in the transverse bore and configured to rest against an outer surface of the first leg and having an eccentric insert bore;

the second threaded portion of the screws configured to penetrate the eccentric insert bore;

wherein the eccentric insert bore causes the screws to have a slanted position relative to the clamp and the stabilizing rod;

clamping nuts configured to engage the second threaded portion and, when tightened on the second threaded portion, forcing the first and second legs of the clamps toward one another thereby securing the stabilizing rod in the receiving bore.

2. The device according to claim 1, wherein the transverse bore of the first leg having the bore insert member inserted therein has a conical shape and tapers in a direction toward the transverse bore in the second leg, and wherein the bore insert member has a conical shape matching the conical shape of the transverse bore of the first leg.

3. The device according to claim 2, wherein the eccentric insert bore is positioned at an acute slant angle relative to a central axis of the conical shape of the bore insert member.

4. The device according to claim 3, wherein the acute slant angle is up to 20°.

5. The device according to claim 2, wherein the transverse bore of the first leg has an inner bore surface with ribbing.

6. The device according to claim 2, wherein the bore insert member has a radial slot extending from the eccentric insert bore radially outwardly to a conical mantle surface of the bore insert member.

7. The device according to claim 6, wherein the slot is positioned at a location where a spacing between the eccentric bore and the conical mantle surface is greatest.

8. The device according to claim 2, wherein the transverse bore of the second leg has a recess diminishing in a direction toward the first bore, wherein the recess is configured to provide a contact surface for the screw head.

9. The device according to claim 8, wherein the screw head has a spherically convex shape and wherein the recess has a spherically concave shape matching the spherically convex shape of the screw head.

10. The device according to claim 1, wherein the bore insert member has a radially projecting rim portion having a support surface resting against the outer surface of the first leg.

11. The device according to claim 10, wherein the outer surface of the first leg has a partially recessed support surface matching the support surface of the bore insert member.

12. The device according to claim 1, wherein the first and second legs have outer leg surfaces facing one another and extending parallel to one another, wherein the outer leg surfaces are positioned at a slant angle, deviating from 90° by up to ±5°, relative to a central bore axis of the receiving bore.

* * * * *